United States Patent [19]

Mochida et al.

[11] Patent Number: 5,552,276
[45] Date of Patent: Sep. 3, 1996

[54] APPARATUS AND PROCESS FOR SIMPLIFIED MEASUREMENT

[75] Inventors: Ei Mochida; Yasuhiko Miyauchi; Takashi Matsuura; Tomoaki Katamine, all of Tokyo, Japan

[73] Assignee: Mochida Pharmaceutical Co., Ltd., Tokyo, Japan

[21] Appl. No.: 207,715

[22] Filed: Mar. 9, 1994

[30] Foreign Application Priority Data

Mar. 18, 1993 [JP] Japan .................................. 5-058707

[51] Int. Cl.⁶ .................................................. G01N 33/543
[52] U.S. Cl. ...................... 435/6; 422/55; 422/56; 422/57; 422/58; 435/7.4; 435/7.5; 435/7.9; 435/7.92; 435/7.93; 435/7.94; 435/174; 435/176; 435/177; 435/179; 435/180; 435/810; 436/164; 436/169; 436/170; 436/172; 436/514; 436/518; 436/524; 436/525; 436/528; 436/530; 436/805; 436/810
[58] Field of Search .................................. 422/55–58, 61, 422/101; 435/6, 7.4, 7.5, 7.9, 7.92, 7.93, 7.94, 7.1, 174, 176, 177, 179–181, 287–289, 291, 805, 810, 970, 973; 436/514, 518, 524, 528, 530, 164, 169, 170, 805, 807, 810, 824, 827, 525, 531, 532–534, 172, 800, 804, 527

[56] References Cited

U.S. PATENT DOCUMENTS

| | | | |
|---|---|---|---|
| 4,254,083 | 3/1981 | Columbus | 422/55 |
| 4,623,461 | 11/1986 | Hossom et al. | 436/137 |
| 4,632,901 | 12/1986 | Valkirs et al. | 422/57 |
| 4,668,472 | 5/1987 | Sakamoto et al. | 422/56 |
| 4,774,192 | 9/1988 | Terminiello et al. | 422/56 |
| 4,916,056 | 4/1990 | Brown, III et al. | 435/805 |
| 4,994,238 | 2/1991 | Daffern et al. | 422/56 |
| 5,006,464 | 4/1991 | Chu et al. | 435/7.92 |
| 5,008,080 | 4/1991 | Brown, III et al. | 422/56 |
| 5,075,078 | 12/1991 | Osikowicz et al. | 422/56 |
| 5,160,701 | 11/1992 | Brown, III et al. | 422/56 |
| 5,166,051 | 11/1992 | Killeen et al. | 422/55 |
| 5,258,163 | 11/1993 | Krause et al. | 422/58 |
| 5,284,622 | 2/1994 | Krause et al. | 422/56 |

FOREIGN PATENT DOCUMENTS

| | | |
|---|---|---|
| 0335244 | 10/1989 | European Pat. Off. . |
| 0452740 | 10/1991 | European Pat. Off. . |
| 62-500121 | 1/1987 | Japan . |
| 1-214760 | 8/1989 | Japan . |
| 3-176659 | 7/1991 | Japan . |
| 3-504166 | 9/1991 | Japan . |
| 4-161853 | 6/1992 | Japan . |
| 4-232861 | 8/1992 | Japan . |
| 4-57226 | 9/1992 | Japan . |
| WO86/01603 | 3/1986 | WIPO . |
| WO86/06978 | 12/1986 | WIPO . |
| WO90/09592 | 8/1990 | WIPO . |

*Primary Examiner*—James C. Housel
*Assistant Examiner*—Christopher L. Chi
*Attorney, Agent, or Firm*—Young & Thompson

[57] ABSTRACT

A simplified measuring apparatus for use in the qualitative or quantitative measurement of substances to be assayed in test samples, such as proteins, antibodies and the like, in a small amount of test samples by a simple and easy operation without requiring a B/F separation step comprises: (a) a liquid permeable porous reaction membrane whose surface having at least one reaction area to which an affinity substance capable of directly or indirectly capturing a substance to be assayed or a soluble agent is immobilized; (b) a porous body arranged on the upper part of the porous reaction membrane, to which a soluble agent capable of being solubilized by the addition of a test sample is adhered in a releasable manner; (c) an absorption member arranged on the lower part of the porous reaction membrane, which contacts with a periphery, excluding the reaction area, of the porous reaction membrane via a liquid non-permeable sheet; (d) a liquid non-permeable transparent cover arranged on the lower part of the absorption member; and (e) a liquid non-permeable case which encloses the foregoing members (a) to (d), having an opening for use in test sample introduction on its top surface and another opening for observation on its under surface.

19 Claims, 4 Drawing Sheets

APPARATUS AND PROCESS FOR SIMPLIFIED MEASUREMENT

FIELD OF THE INVENTION

This invention relates to an apparatus for effecting a quick and simplified measurement in which a porous reaction membrane is employed, and to a measuring process making use thereof.

BACKGROUND OF THE INVENTION

Measurement of minor constituents in the living body has been used frequently for many purposes such as diagnosis of various diseases and judgement of therapeutic effects. Presently, such measurement is carried out not only at medical facilities but also domestically by unskilled persons in many cases. Depending on each purpose, diagnostic drugs are properly used in an accurate measuring method having high sensitivity and high accuracy or in a simplified measuring method which is easy to handle and can show results in a short time. In particular, since the simplified measuring method does not require a reaction apparatus, a measuring instrument and the like and is easily practiced by simple handling, it is considerably handy when the diagnosis can be made only by a semi-quantitative or qualitative measurement. Because of this, the simplified measuring method is used broadly for the diagnosis of pregnancy and the like.

With regard to the immunoassay, several simplified methods are now commonly used which include for example an agglutination reaction or an agglutination inhibition reaction in which latex is used as a carrier, an enzyme immunoassay (EIA) in which an enzyme is used as a label and a simplified immunological measuring method in which colloidal non-metal particle or colored latex is used as a label.

In recent years, methods in which porous reaction membranes are utilized have been broadly used as simplified immunological measuring methods. Almost all such methods use colored substances directly conjugated to antibodies, unlike the case of EIA in which substrates for respective enzymes are used in the coloring process. The use of such methods has rendered possible further simplified operation and shortened assay period in comparison with other prior art techniques including the latex-aided agglutination or agglutination inhibition reaction and EIA.

Illustrative examples of the process and measuring apparatus for use in such a type of simplified immunological measuring method are those disclosed in JP-A-3-504166 and JP-A- 3-176659 (the term "JP-A" as used herein means an "unexamined published Japanese patent application"). In these methods, a porous reaction membrane is used as a chromatograph strip, a reagent is set on a specified area on the surface of the strip and the reaction is effected by allowing the reagent to migrate together with a test sample in accordance with the principle of chromatography. These methods, however, have a disadvantage in that a relatively long reaction time is required to complete migration of the reagent and test sample through a certain distance on the chromatograph strip.

Contrary to these methods in which a test sample is made to flow in a horizontal direction, the following examples make a test sample flow in a vertical direction.

JP-A-62-500121 discloses a reaction apparatus in which a soluble agent-included porous body is arranged on the upper part of an affinity substance-immobilized porous reaction membrane, the soluble agent is solubilized by the addition of a test sample, thereby allowing the resulting liquid to pass through the affinity substance-immobilized porous reaction membrane, and the liquid is absorbed into a liquid absorbing zone connected to the lower part of the membrane.

JP-A-4-161853 discloses a process in which gold colloid is used as a soluble agent, a porous and elastic member having functions both to adhere the soluble agent and to absorb a test sample solution is arranged on the lower part of an affinity substance-immobilized porous reaction membrane and the signal after completion of the reaction is observed by separating a container. Since the signal was not so clear, a modified process has been disclosed in JP-A-4-232861 in which an enzyme-labeled antibody and its corresponding substrate were used for color development.

There are a number of disclosures relating to such type of apparatus and process in which a test sample is allowed to pass through a porous reaction membrane in a vertical direction, but each of them requires a step to separate or open a part of its apparatus to observe the signal.

As an example of a measuring apparatus which does not require separation or opening of its part when the signal is measured, is JP-B-4-57226 (the term "JP-B" as used herein means an "examined Japanese patent application") which discloses a reaction apparatus comprising an upper structure designed in such manner that a reaction solution falls only on a reaction zone at the center of a filter and a lower structure designed in such manner that the reaction solution thus concentrated on the restricted reaction zone at the center of the filter flows through the filter in a horizontal direction toward its periphery and is absorbed by an absorbing body located adjacent to the upper or lower part of the peripheral area. Since the lower part of the filter is made into an enclosing container having a window, the signal can be read from the bottom surface through the window. Though this process has an advantage in that the signal can be observed easily by simply turning over the reaction apparatus after completion of the reaction, it also has several disadvantages. Specifically since the reaction apparatus itself is not designed for a simple and quick measurement by a one step operation, it is necessary to carry out preliminary treatments such as filtration of test samples, immunological reactions and the like in a separate reaction vessel. This vessel is subsequently attached as such to an inlet of the above reaction apparatus to introduce the resulting reaction solution into the apparatus, thus causing problems in that it requires complex handling for a simplified measuring apparatus and is too time-consuming to obtain the results. In addition, this process has another disadvantage in that the measuring apparatus must be constructed in a precise manner which entails complex structure, because it is necessary to effect migration of the reaction solution concentrated on the restricted reaction zone at the center of the filter toward the periphery of the porous reaction membrane based on the principle of chromatography.

In order to obtain results by a simple one step operation using a simplified measuring apparatus, one must take a special precaution to carry out sufficient B/F separation (for example in an antigen-antibody reaction, physical separation of a bound type "B" resulting from binding an antigen and an antibody and a free type "F" without a binding). In other words, it is necessary to remove the remaining-unreacted reagents such as labelled antibody from the judging area of a simplified measuring apparatus by various means, in order to prevent visual obstruction. The process disclosed in JP-A-1-214760 requires complex handling because the disclosure states that the porous reaction membrane should be washed with water, a buffer or the like as occasion demands.

Also, the simplified immunological measuring method to which the principle of chromatography is applied requires a considerably long time to complete the reaction, because washing for the B/F separation after reaction on the porous reaction membrane is effected by supplying an excess volume of each test sample containing a substance to be assayed. In addition, in the case of the processes in which each of the test sample is allowed to migrate in a vertical direction, they have an advantage in that the reaction time is generally shorter than in the case of a horizontal migration. However, as described in the foregoing, most of them require an operational step for the detachment of a part of the apparatus or drawing out of a judging part as a unit in order to carry out visual judgement. Such an operation results in a possible danger of causing contact of hands and a part of the body with blood, urine and the like used as test samples.

It is necessary to obtain results precisely in a short time not only in the simplified measuring method for diagnosis of pregnancy but also in all of the simplified measuring methods, even if the unskilled person performs the method. The important objects of the measuring method are low cost, quickness and simplicity.

There are a number of simplified measuring apparatuses and processes which uses porous reaction membranes, but many of them do not have the simplicity and accuracy required for the simplified measurement due to the aforementioned disadvantages such as a time-consuming reaction, a plurality of operation steps, a complex container structure, an unclear image to be judged and the like. Since one of the important factors which affects the rapidity and simplicity of the measurement is simple and accurate performance of B/F separation, a great deal of effect has been directed toward the development of simplified measuring apparatus and process which do not require the B/F separation as a special independent operation step. By overcoming these problems involved in the prior art, results of the simplified measurement will be obtained more accurately within a shorter assay period by a simpler operation.

Accordingly, the present invention contemplates providing a simplified measuring apparatus by which measurement can be made with a simple one step operation without employing a B/F separation step as a specific operation.

SUMMARY OF THE INVENTION

With the aim of overcoming the aforementioned problems involved in the prior art, the inventors of the present invention have conducted intensive studies seeking for a measuring system by which accurate results can be obtained in a short time with a simple one step operation and, as a result, found a measuring apparatus wherein a porous body to which a soluble agent capable of being solubilized by the addition of a test sample is adhered is arranged on the upper part of an affinity substance-immobilized porous reaction membrane. The soluble agent solubilized by the addition of the test sample and a substance to be assayed contained in the test sample are allowed to react with the affinity substance immobilized on the porous reaction membrane, unreacted and excess reacted solutions passed through the porous reaction membrane are absorbed by an absorption member arranged on the lower part periphery of the porous reaction membrane. The contacting surface of the absorption member to the porous reaction membrane is liquid non-permeable and the lower part of the absorption member has a liquid non-permeable transparent cover, and the resulting signal is observed from an opening on the under surface of the apparatus. The present invention has been accomplished on the basis of this finding.

Particularly, according to the present invention, there is provided a simplified measuring apparatus which comprises (a) a liquid permeable porous reaction membrane whose surface has at least one reaction area to which an affinity substance capable of directly or indirectly capturing a substance to be assayed or a soluble agent is immobilized, (b) a porous body arranged on the upper part of the porous reaction membrane, to which a soluble agent capable of being solubilized by the addition of a test sample is adhered in a releasable manner, (c) an absorption member arranged on the lower part of the porous reaction membrane in such a manner that it contacts with a periphery, excluding the reaction area, of the porous reaction membrane via a liquid non-permeable sheet, (d) a liquid non-permeable transparent cover arranged on the lower part of the absorption member and (e) a liquid non-permeable case which encloses the above members (a) to (d), having an opening for introducing a test sample on its top surface and another opening for observation on its under surface. In this instance, the term "top surface" or "upper part" means upstream direction of the flow of a test sample, and the term "under surface" or "lower part" means downstream direction of the sample flow.

Preferably, the aforementioned reaction area comprises a plurality of reaction sites having different affinity materials immobilized thereto. Also preferably, the plural reaction sites having different affinity substances immobilized thereto are separated from one another.

Preferably, the aforementioned affinity substance immobilized on the porous reaction membrane is an antibody or an antigen. Also preferably, the affinity substance immobilized on the porous reaction membrane is a nucleic acid, lectin, biotin, avidin, an enzyme, an inhibitor or a receptor.

Preferably, the aforementioned soluble agent is an antibody or an antigen, which is labeled with a marker to render possible detection of the agent. Also preferably, the soluble agent is a nucleic acid, lectin, biotin, avidin, an enzyme, an inhibitor, a receptor or a derivative of a substance to be assayed, which is labeled with a marker to render possible detection of the agent.

Preferably, the aforementioned marker is a substance selected from enzymes, fluorescent compounds, radioactive markers, chemiluminescent compounds, colloidal metal particles, non-metal particles, dye particles and latex particles.

Preferably, the aforementioned porous reaction membrane is selected from cellulose, a cellulose derivative, nitrocellulose, a porous synthetic polymer, a glass fiber filter and cloth.

Preferably, the aforementioned porous body to which a soluble agent is adhered in a releasable manner is selected from cellulose, a cellulose derivative, a porous synthetic polymer, a glass fiber filter, a non woven fabric and cloth.

Preferably, the aforementioned absorption member is selected from cellulose, a cellulose derivative, a porous synthetic polymer, a glass fiber filter, a non woven fabric, a granular absorbent and cloth.

Preferably, the porous reaction membrane is nitrocellulose and the absorption member and the porous body are both cellulose.

In addition, the aforementioned reaction area of the porous reaction membrane may be subjected to washing.

Preferably, the aforementioned test sample is a body fluid or a solution obtained by diluting or extraction-diluting biological components.

Also provided by the present invention is a measuring process for the detection of the presence and quantity of a substance to be assayed contained in test samples making use of the aforementioned simplified measuring apparatus, which comprises;

(a) adding a test sample having a possibility of containing a substance to be assayed to the opening for introducing test sample on the top surface of the case, thereby effecting solubilization of a soluble agent adhered in a releasable manner to the porous body and subsequent migration of resulting solution to the porous reaction membrane, (b) allowing the test sample, the soluble agent or a complex thereof in the reaction solution to contact with and linked to an affinity substance immobilized to the reaction area on the porous reaction membrane, thereby effecting formation of detectable signal directly or indirectly, (c) allowing resulting reaction residue to pass through the porous reaction membrane from its top surface to under surface and then to be absorbed by the absorption member, and (d) observing the signal from the opening on the under surface of the case.

Other objects and advantages of the present invention will be made apparent as the description progresses.

DETAILED DESCRIPTION OF THE INVENTION

Figure 1:
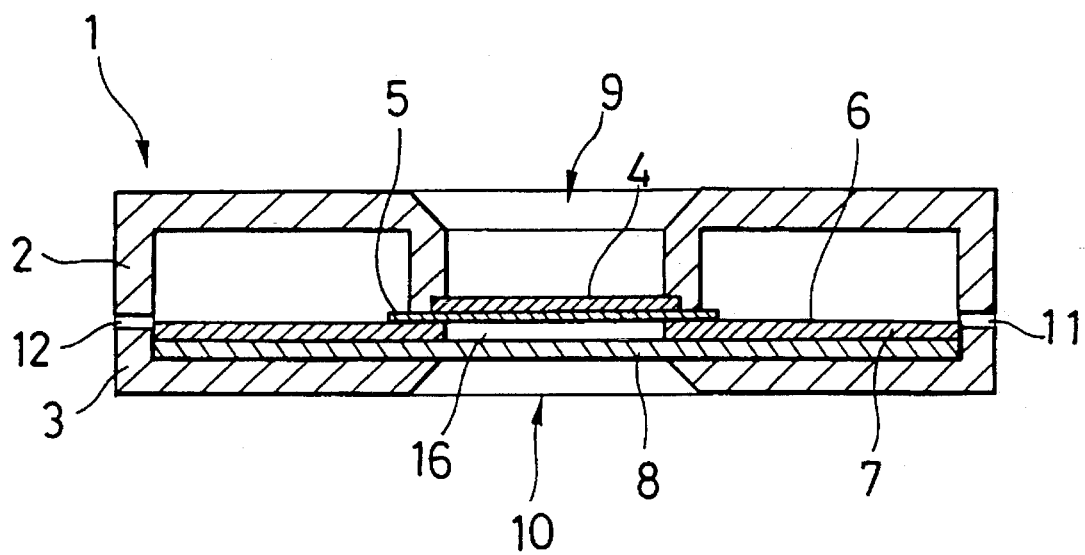
FIG. 1 is a partial sectional view of the measuring apparatus of the present invention.

The measuring apparatus of the present invention has a simple structure and can produce results quickly and easily. In other words, according to this measuring apparatus, a test sample is passed in a vertical direction through a porous reaction membrane having a reaction area to which an affinity substance is immobilized, resulting reaction solution is absorbed by an absorption member which is in contact with the periphery, excluding the reaction area, of the porous reaction membrane and then the resulting signal is observed from the under surface of the container with the naked eye or quantitatively using an instrument. In general, when a reaction solution is passed through a porous reaction membrane a vertical direction, an absorption member is arranged directly under the porous reaction membrane. In such a known structure, the signal formed as the result of the reaction cannot be observed directly because its reaction area is concealed by the absorption member, a test sample-filtering medium and the like.

In the case of the present invention, the absorption member is arranged under the reaction area of the porous reaction membrane not directly but with a certain space so that the reaction solution passed through the porous reaction membrane is temporarily stored in the space under the porous reaction membrane and then absorbed by the absorption member.

Also, in order to prevent absorption of unreacted solution and excess reaction solution by the absorption member without passing through the reaction solution-storage space under the porous reaction membrane, a liquid non-permeable sheet is interposed between the absorption member and the porous reaction membrane. In addition, the under surface of the absorption member is protected with a liquid non-permeable transparent cover in order to prevent scattering of the reaction solution passed through the porous reaction membrane. An observation window is arranged on the under surface of a case in which the above parts are enclosed, so that the signal on the reaction area of the porous reaction membrane can be observed from the under surface of the measuring apparatus after completion of the reaction, either with the naked eye or using an instrument. A porous body to which a soluble agent capable of being solubilized by the addition of a test sample is adhered is arranged on the top surface of the porous reaction membrane, and each of these parts is enclosed in the liquid non-permeable case having openings on its top and under surfaces. Development of such a construction has rendered possible simple measuring operation with only one step for the introduction of each test sample. That is, since test results can be obtained simply by introducing a test sample from the top surface of the measuring apparatus and, after completion of the reaction, turning the apparatus over to observe the resulting signal from its back side, the measurement does not require any other operation such as to detach a part of the container or pull out the porous reaction membrane for the observation of the signal. Such a construction of the inventive measuring apparatus can also exclude another prior art problem of causing contact of hands and a part of the body with test samples during the operation. Because of the markedly simple structure, the measuring apparatus of the present invention can be produced at a low cost without having the aforementioned problems involved in the prior art.

When compared with the measuring apparatus disclosed in JP-B-4-57226 which does not require operation for the separation or opening of its part during the signal observation, the measuring apparatus of the present invention can be produced without making it into a complex structure and can complete the reaction in a short time, because it is not necessary to make the reaction solution concentrated in the restricted reaction zone on the filter center to migrate toward the periphery of the porous reaction membrane based on the principle of chromatography.

In addition, since the measuring process of the present invention can make the reaction solution, as a mixture of the soluble agent and a test sample, to contact in a uniform state with the reaction area on the porous reaction membrane, it is possible to unify signal strength of each part of the reaction area. In other words, semi-quantitative or quantitative measurement can be made by arranging a plurality of signals as controls for the measurement on the reaction area together with the signal for the test sample measurement and comparing their signal strengths. Also, the uniform signal strength on the reaction area results in another advantage in that signal design can be made at will.

Examples of the porous reaction membrane to be used in the present invention include cellulose, a cellulose derivative, nitrocellulose, a porous synthetic polymer such as a nylon membrane or the like, a glass fiber filter, cloth and the like.

These porous reaction membranes should have pores which communicate their top and under surfaces and have a pore size large enough for an unreacted soluble agent to pass through the communicating pores. In general cases, such a pore size may be in the range of preferably from 1 to 10 microns, more preferably from 3 to 10 microns.

An affinity material which will be described later in detail is immobilized on the porous reaction membrane.

Immobilization of an affinity material on the porous reaction membrane can be effected in the usual way. For example, when the porous reaction membrane is nitrocellulose, immobilization may be effected by applying a desired amount of an affinity substance solution to nitrocellulose and, after drying at 37° C., blocking unbound portions with albumin or the like.

The amount of affinity substance to be immobilized on the porous reaction membrane varies depending on the type of substance to be assayed and the affinity substance used, but it may preferably be in the range of approximately from 0.03 to 20 µg/cm².

Preferably, the affinity substance may be immobilized on the porous reaction membrane in an easily recognizable plain shape such as a cross, parallel lines, a circle, a double circle, a star, a triangle, a simple illustration or the like.

Examples of the porous body to be used in the present invention, to which a soluble agent is adhered in a releasable manner, include cellulose, a cellulose derivative, a porous synthetic polymer, a glass fiber filter, a non woven fabric, cloth and the like. Since the porous body is used herein to filter each test sample and to quickly solubilize and release the soluble agent adhered thereto by the addition of the test sample, it is desirable to select its substance based on its compatibility with the substance to be assayed and measuring reagent. The soluble agent to be adhered to the porous body will be described later in detail. When a soluble agent-adhered porous body is produced, it is desirable to carry out freeze-drying in the presence of salt, sugar, protein and the like in order to improve its stability. Also, a surface-active agent can be added as a dispersing agent for the purpose of improving solubility of a soluble agent at the time of its solubilization by the addition of a test sample.

Examples of the absorption member to be used in the present invention include cellulose, a cellulose derivative, a porous synthetic polymer, a glass fiber filter, a non woven fabric, a granular absorbent such as a copolymer of methyl methacrylate and vinyl acetate, cloth and the like. The absorption member should have a certain thickness of preferably from 0.2 to 1.5 mm, more preferably from 0.5 to 1.2 mm, in order to ensure a certain space created by the thickness under the reaction area of the porous reaction membrane. It is possible to control absorption rate of the reaction solution by selecting suitable construction material of the absorption member. By slowing down the absorption rate, contact time of the reaction solution with the reaction area of the porous reaction membrane can be lengthened, which renders possible alteration of the measuring sensitivity. Also, in order to prevent absorption of unreacted solution and excess reaction solution by the absorption member without passing through the reaction solution-storage space under the porous reaction membrane, the porous reaction membrane-contacting surface of the absorption member is laminated or sealed with a liquid non-permeable material such as polyethylene.

The transparent cover to be used in the present invention may be prepared from a material preferably having high light transmittance, smooth surface and uniform liquid wettability (or water repellency), such as glass, acrylic resin, polycarbonate, vinyl chloride or the like. The transparent cover may have a thickness of preferably from 0.1 to 2.0 mm, more preferably from 0.2 to 1.5 mm. The transparent cover may be adhered to the under surface of the absorption member, adhered to the inner surface of a case having a judging area on its under surface or interposed between the absorption member and the case. It is desirable that the transparent cover material has high light transmittance and is uniform in quality because, according to the present invention, the signal can be observed not only by the naked eye but also using an optical instrument which renders possible quantitative measurement.

The enclosing case to be used in the present invention is a container which encloses the aforementioned porous reaction membrane, porous body, absorption member and transparent cover, having an opening for introducing the test sample on its top surface and another opening for observation on its under surface, and it may be produced from any construction material, provided that it is liquid non-permeable, but preferably from a resin in view of processability and profitability.

In an alternative case, the measuring apparatus of the present invention may not require the enclosing case, provided that the aforementioned parts are made into an integrally bonded body which is rather useful in quantitatively or semi-quantitatively measuring the signal by integrating it into a measuring device such as an instrument that optically measures concentration of signals. In that case, the measuring apparatus of the present invention can be used without the enclosing case, provided that the main body consisting of the porous reaction membrane, porous body, absorption member and transparent cover is stably fixed with a splicer and the like.

Though the measuring apparatus of the present invention is devised as a simplified measuring apparatus by which the results can be judged by the naked eye, it can be used not only for qualitative measurement but also for semi-quantitative or simplified quantitative measurement. Shapes of the signal on the reaction area are described in the foregoing. Semi-quantitative measurement can be made by binding a predetermined concentration of a standard substance to a moiety of the signal and comparing signal strength of a substance to be assayed with that of the standard substance. Also, it is possible to effect quantitative determination by measuring strength of the signal on the reaction area using an appropriate optical instrument. For example, semi-quantitative or simplified quantitative measurement can be made by immobilizing a substance to be assayed with varied concentrations as standards in the form of dots on the reaction area of the porous reaction membrane, immobilizing an antibody specific for the substance to be assayed, as a test sample-measuring agent, on the same reaction membrane in the form of dots having the same size as the substance to be assayed, and comparing their signal strengths.

Sandwich type and competitive type measurements can be applied to the measuring process of the present invention in which the aforementioned simplified measuring apparatus is used. When sandwich type measurement is applied, the signal strength increases in proportion to the concentration of a substance to be assayed. When competitive type measurement is applied, the signal strength decreases in proportion to the concentration of a substance to be assayed. By comparing this signal strength with that of a standard substance, the presence or amount of a substance to be assayed can be determined.

The test sample to be used in the simplified measuring apparatus and measuring process of the present invention is a body fluid or a diluted or extraction-diluted solution of biological components, having a possibility of containing a substance to be assayed. Illustrative examples of such test samples mainly include blood, plasma, serum, urine, saliva, lymph, vaginal discharge, milk, nipple discharge, seminal fluid, intracystic fluid, fecal extract, tissue extract and the like.

The substance to be assayed is a substance to be detected qualitatively or quantitatively by the measuring apparatus of the present invention, with its illustrative examples including various proteins and peptides which exert their function as antigens or antibodies, nucleic acids, effector molecules, receptor molecules, enzymes, coenzymes, inhibitors, sugar chains and lipids or compounds containing them, lectin and other biological substances, drugs, drug metabolites and the like, more particularly, human chorionic gonadotropin (hCG), lutenizing hormone (LH), α-fetoprotein (AFP), carcinoembryonic antigen (CEA), human placental lactogen (hPL), $\beta_2$ microglobulin ($\beta 2m$), ferritin, Hepatitis B surface (HBs) antigen, estrogen, anti-HBs antibody, anti-Human immunodeficiency virus (HIV) antibody, IgE antibody, anti-rubella antibody and the like.

Results of the measurement of various substances to be assayed are judged normal or abnormal based on the comparison with their physiological concentrations. For example, in the case of the diagnosis of rupture of the membranes, AFP in vaginal content is measured as a means to confirm the presence of amniotic fluid in the vaginal content, because AFP as a normal component of the amniotic fluid is mixed in the vaginal content when the amniotic fluid leaks into vagina caused by rupture of the membranes. The substance to be assayed according to the present invention includes such substances.

The affinity substances and the soluble agent to be used in the present invention are substances which show affinity for the substance to be assayed directly or via an affinity substance, with their illustrative examples including various proteins and peptides which exert their function as antigens or antibodies, nucleic acids, lectin, biotin, avidin, enzymes, inhibitor, receptors, sugar chains or compounds containing the sugar chains, drugs, drug metabolites, derivatives of each substance to be assayed and the like, more particularly, the antibodies specific for human chorionic gonadotropin (hCG), lutenizing hormone (LH), α-fetoprotein (AFP), carcinoembryonic antigen (CEA), human placental lactogen (hPL), $\beta_2$ microglobulin ($\beta 2m$), ferritin, HBs antigen, estrogen and the like.

The soluble agent to be used in the present invention is labeled by binding with a marker substance through physical adsorption such as hydrophobic bonding, or chemical bonding such as covalent bonding.

The thus labeled soluble agent is adhered to the porous body in such a manner that it is released easily caused by a test sample. The adhesion can be effected by soaking the porous body in a soluble agent-containing solution, followed by drying. The drying may be effected most preferably by freeze-drying, because it can distribute the agent to be adhered quickly and uniformly.

The affinity substance to be used in the present invention is immobilized on the porous reaction membrane through physical adsorption such as hydrophobic bonding or chemical bonding such as covalent bonding.

The affinity substance to be used in the present invention is immobilized on the reaction area of the porous reaction membrane by a procedure usually used for the immobilization of affinity substances, in such a manner that the immobilized affinity substance is not released when a test sample is passed through the membrane. For example, the immobilization may be effected by applying the affinity substance to the reaction membrane and then heating the thus treated membrane.

Examples of the marker to be used in the present invention include enzymes or substrates, fluorescent compounds, radioactive markers, chemiluminescent compounds, colloidal metal particles, non-metal particles, dye particles, latex particles, chromogens, catalysts, liposomes and the like, of which enzymes, fluorescent compounds, radioactive markers, chemiluminescent compounds, colloidal metal particles, non-metal particles, dye particles and latex particles are particularly preferred.

The amount of the marker to be labeled on the soluble agent varies depending on the types of the used soluble agent and marker. For example, when anti-hCG antibody is used as the soluble agent and a disperse dye is used as the marker, 0.3 to 30 mg/ml of the disperse dye may be used based on 0.5 mg/ml of the antibody, at a final concentration in a mixture prepared by adding a solution of the disperse dye to a solution of the antibody. In this case, a preparation of a disperse dye-labeled antibody as a labeled soluble agent may be obtained for example by incubating the disperse dye and the antibody at 56° C. for 30 minutes, subjecting the resulting mixture to 10 minutes of centrifugation at 22,000×g after 20 minutes of cooling on an ice bath and then suspending the thus obtained precipitate in an albumin/lactose/PBS solution.

Amounts of the soluble agent to be adhered to the porous body and the affinity substance to be immobilized on the porous reaction membrane may be arbitrarily decided depending on the criterion of each substance to be assayed.

The following describes the present invention further in detail with reference to preferred examples shown in the drawings. It is to be understood, however, that the following description is for purpose of illustration only and is not intended as a definition of the limits of the present invention. In the following description on the measuring process of the present invention, the term "upper part" or "lower part" means upper or lower part in gravitational direction when the apparatus is set on a horizontal plane in the case of introducing test samples into the simplified measuring apparatus of the present invention.

Figure 2:
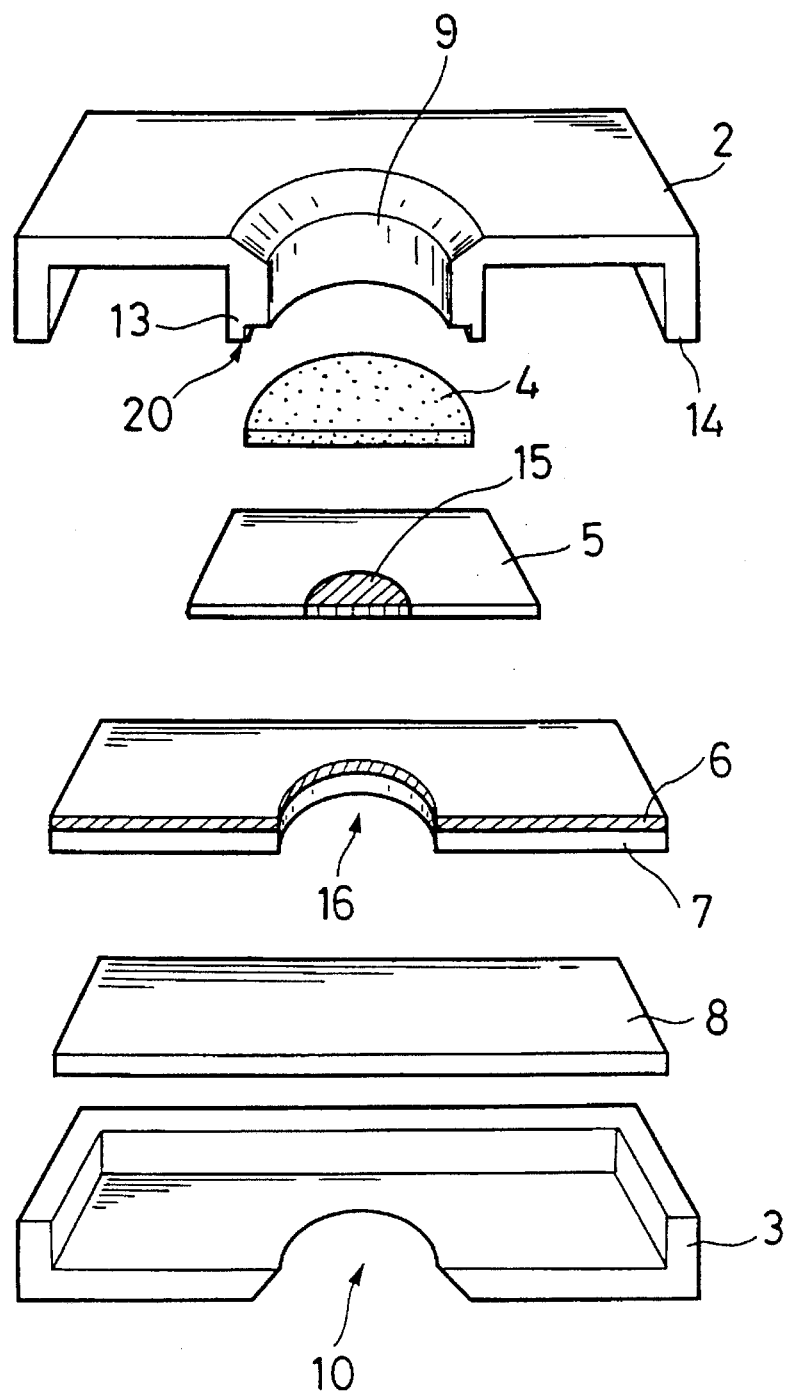
FIG. 2 is a partial sectional exploded perspective view of the measuring apparatus of the present invention.

The simplified measuring apparatus 1 of the present invention shown in FIG. 1 comprises an opening 9 for introducing a test sample, a porous body 4, a porous reaction membrane 5, a liquid non-permeable sheet 6, an absorption member 7, an opening 10 for observation and cases 2 and 3. FIG. 2 is an exploded perspective view of the simplified measuring apparatus of FIG. 1.

The opening 9, provided in the case 2, is used for the introduction of test samples and has a volumetric capacity large enough to keep the introduced sample temporarily so that the added test sample does not leak out of the apparatus until it passes through the porous body 4. Consequently, the opening 9 may have a capacity of preferably from 0.1 to 2 ml.

The porous body 4 is a porous carrier which removes impurities in test samples and to which a soluble agent capable of binding a substance to be assayed is impregnated to adhere. The porous body should have pores of such a size that flow rate of each test sample can be controlled at a level which is sufficient enough to complete the binding of each substance to be assayed and the soluble agent, and that the resulting complex body of the substance to be assayed and the soluble agent can pass through the pores. The pore size may be preferably in the range of from 0.5 to 500 μm, though it may vary depending on the type of the substance to be assayed and the soluble agent.

The porous reaction membrane 5 is a porous membrane, made of nitrocellulose or the like, which has a reaction area 15 on its central portion.

The reaction area 15 makes an affinity substance capable of binding each substance to be assayed or the soluble agent directly or indirectly, immobilized on its surface, and at least one reaction area is contained in the measuring apparatus of the present invention.

The liquid non-permeable sheet 6 is used to prevent from passing each substance to be assayed and the soluble agent or a complex body thereof without binding to the reaction area 15, caused by direct absorption of a test sample by the absorption member 7 arranged on the downstream side of the sheet in a horizontal direction from the porous reaction membrane 5 arranged on the upstream side of the sheet when the test sample is applied.

The absorption member 7 is arranged on the downstream side of the liquid non-permeable sheet 6, and is a member to be used for the absorption of a test sample containing unreacted soluble agent passed through the porous reaction membrane 5 when a test sample is applied. In order to enable observation of the reaction area 15 after completion of the reaction, the absorption member 7 has reaction solution-storing space 16 which is obtained by cutting out a portion of the absorption member 7 arranged on the downstream side of the reaction area 15 in a cylindrical shape having a concentric circle with the observation opening 10. The reaction solution storing space 16 can temporarily store a test sample flowed therein to effect stable reaction.

A transparent cover 8 is arranged on the downstream side of the absorption member 7, and is made of a liquid non-permeable material in order to prevent leakage of test samples from the simplified measuring apparatus.

The aforementioned porous body 4, the porous reaction membrane 5, the liquid non-permeable sheet 6, the absorption member 7 and the transparent cover 8 are securely fixed and enclosed with the cover 2 having the opening 9 for introducing test samples and the case 3 having the observation opening 10.

The simplified measuring apparatus 1 has a construction in which the case 2 having the opening 9 for introducing test samples and the case 3 having the opening 10 for observing the signals are interlocked with a joint part 11.

Appearance of the simplified measuring apparatus 1 may be selected at will, such as cylindrical, square, rectangular, long cylindrical and the like shapes.

Preferably, the joint part 11 or the case 3 may have a hole 12 for discharging air.

The lower part of the opening 9 is provided with a level-difference 13 for arranging the porous body 4 to which the soluble agent is adhered without any slippage and disengagement. The porous reaction membrane 5 is closely interposed between the porous body 4 and the absorption member 7 whose top surface is coated with the liquid non-permeable sheet 6.

When the cases 2 and 3 are interlocked, the porous body 4, the porous reaction membrane 5, the liquid non-permeable sheet 6, the absorption member 7 and the transparent cover 8 are held between the cases 2 and 3 so tightly that these members are kept immobile in the case.

Consequently, when the simplified measuring apparatus 1 is set in a horizontal direction, the aperture of the opening 9 for introducing a test sample has the same central axis in gravitational direction with the aperture of the observation opening 10 from which the signal is observed via the porous body 4 and the reaction area 15 on the porous reaction membrane 5. Furthermore, the observation opening 10 may have an aperture diameter which is large enough for observing the shapes of the cross, triangle or the like on the reaction area 15. The measuring apparatus of the present invention is constructed such that a test sample introduced into the opening 9 passes through the porous body 4 and the porous reaction membrane 5 in order by gravitational force and is absorbed by the absorption member 7 through the reaction solution storing space 16.

In order to adhere the porous body 4 and the porous reaction membrane 5 without gaps and to keep the porous reaction membrane 5 immobile when the case 2 and the case 3 are interlocked, a terminal point 20 of the level-difference 13 provided in the case 2 to keep the porous body 4 protruded at a level slightly longer that an outside terminal point 14 of the case 2.

Protruded portion of the terminal point 20 of the level-difference 13 may have a length of preferably from 0.1 to 1.5 mm, more preferably from 0.2 to 1.0 mm, though it varies depending on the construction materials of the porous body 4 and the absorption member 7.

Each member constituting the measuring apparatus may have any optional shape such as circle, square, rectangle or the like corresponding to the shapes of the case 2 and the case 3.

Since only the top surface of the absorption member 7 is liquid non-permeable, an application of the liquid non-permeable sheet 6 on the top surface of the absorption member 7 may be formed by an adhesion treatment with a liquid non-permeable synthetic polymer sheet, a laminating or a coating such as a silicon treatment. Preferably, it may be effected by a polyethylene or polypropylene laminating.

According to the simplified measuring apparatus of the present invention, a reaction solution is passed through the porous reaction membrane 5 in a vertical direction and then absorbed by the absorption member 7 adhered closely at the periphery of the reaction area 15, and a portion of the absorption member 7 and liquid non-permeable sheet 6, which corresponds to the lower part of the reaction area 15, has the reaction solution storing space 16 having a size identical with or similar to the size of the reaction area 15.

Though the shape of the reaction area 15 is substantially circular, any other shape may be used. When the reaction area 15 has a circular shape, it is desirable that the portion cut from the absorption member 7 (reaction solution storing space 16) has a cylindrical shape of the same diameter.

In the reaction solution storing space 16, a test sample passed through the porous reaction membrane 5 is temporarily stored to ensure sufficient binding of a complex of a substance to be assayed and its soluble agent to an affinity substance in the reaction area 15. Thereafter, the test sample is absorbed by the absorption member 7 and discharged from the reaction solution storing space 16.

In order to keep certain space under the reaction area 15, the absorption member 7 may be prepared preferably from a hard raw material such as a filter paper, a glass fiber filter, a porous hydrophilic polymer or the like. Volume of the reaction solution to be absorbed by the absorption member 7 can be controlled by the thickness and area of the absorption member 7. In the case of a simplified measurement for use in the diagnosis of pregnancy or the like, the absorption member 7 may have an absorption capacity of approximately 1 ml and an area of 16 cm² when Toyo filter paper No. 28 is used. Optionally, the absorption member 7 may have a groove for use in the discharge of air.

The transparent cover 8 is used also as a flow passage of the reaction solution passed through the porous reaction membrane 5 and trickled down on the central part of the transparent cover corresponding to the window formed by the opening of the underside case, where the trickled reaction solution spreads on the surface of the transparent cover from its central part toward its periphery until the solution contacts with the absorption member 7 to be absorbed thereby. In consequence, it is desirable to select a material having smooth surface and uniform liquid wettability. It is desirable also to use an optically transparent and homogeneous material, because the signal can be measured using an optical instrument as described in the foregoing.

Figure 3:
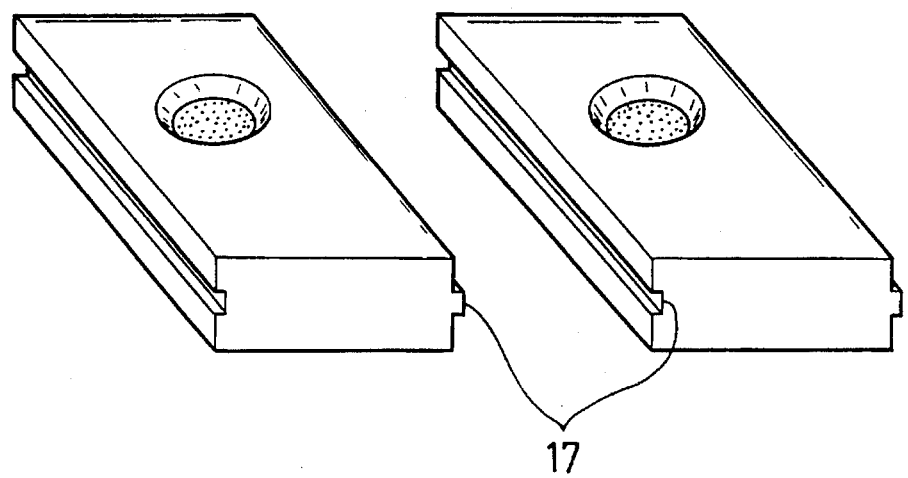
FIG. 3 is a perspective view showing another example of the present invention in which independent measuring apparatuses are used in combination to measure a plurality of assay items.

FIG. 3 shows another example of the simplified measuring apparatus of the present invention in which a plurality of the measuring apparatus are used in combination, thus rendering possible measurement of plural substances to be assayed in the same test sample, as well as semi-quantitative or quantitative determination by the simultaneous measurement of a test sample and a standard substance. The enclosing case of each apparatus may be provided with a connecting part 17 for fixing which can connect each measuring apparatus with a possibility of attaching and removing.

Figure 4:
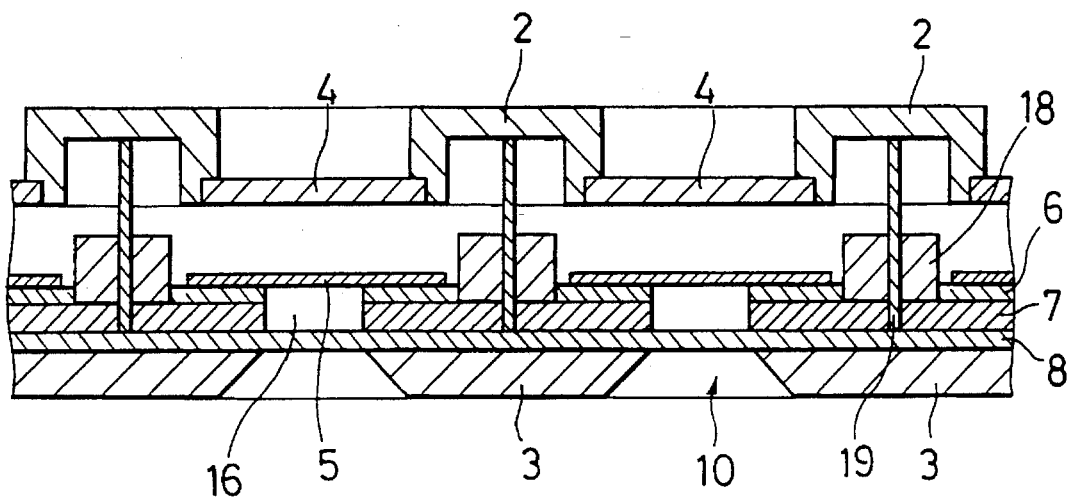
FIG. 4 is a sectional view showing still another example of the present invention in which a plurality of independent measuring parts are included in a single measuring apparatus.
Figure 5C:
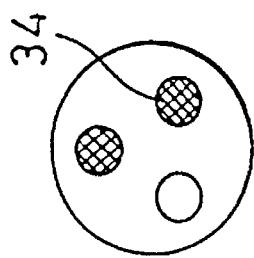
FIG. 5(a) shows a bottom plan view of the measuring apparatus and FIGS. 5(b)–5(g) depict examples of signals.
Figure 5D:
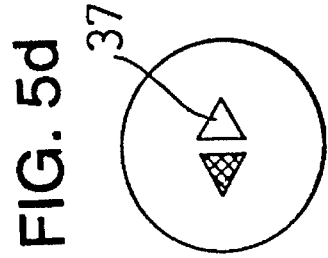
Figure 5F:
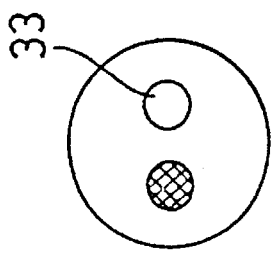
Figure 5G:
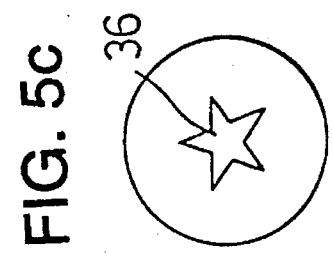
Figure 5B:
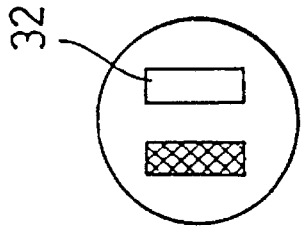
Figure 5E:
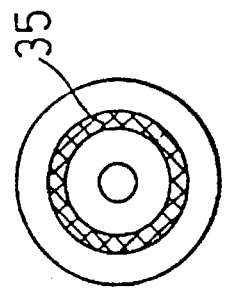
Figure 5A:
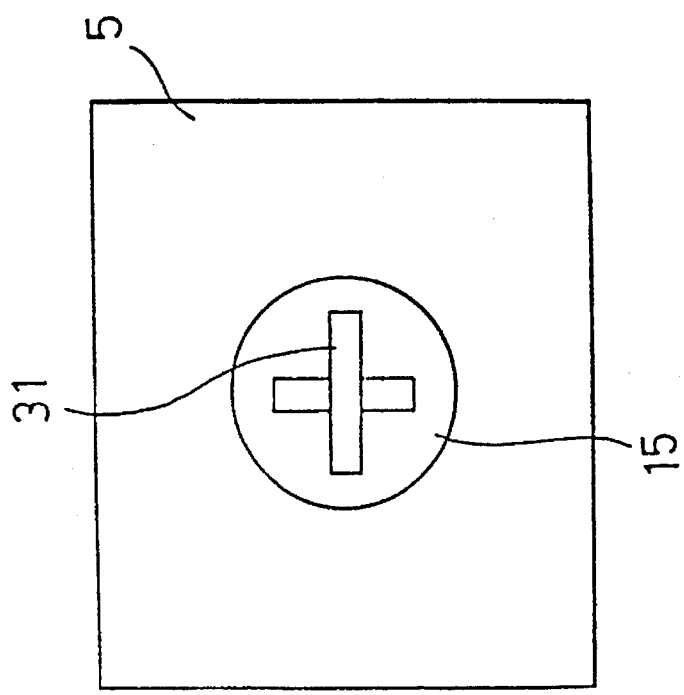

FIG. 4 shows still another example of the simplified measuring apparatus of the present invention in which a plurality of the measuring apparatus are enclosed in a single case. This apparatus is useful for the semi-quantitative or quantitative determination by the simultaneous measurement of a test sample and a standard substance, in which the distance between the observation openings 10 is shortened to effect easy observation of signals of the test sample and standard substance when they are compared.

That is, in order to reduce the area of the absorption member 7, while simultaneously increasing capacity of the absorption member 7 to absorb the reaction solution passed through the porous reaction membrane 5, an absorption auxiliary member 18 is arranged directly on the top surface of the absorption member 7 making use of the space in the case 2, without the liquid non-permeable sheet 6 interposed between the contacting surfaces of the porous reaction membrane 5 and the absorption member 7. When sufficient reaction solution absorbing capacity cannot be obtained by changing the thickness and area of the absorption member 7, such a direct arrangement of the absorption auxiliary member 18 may be used effectively.

In order to avoid contamination of other test sample from the adjacent reaction area, two of the absorption auxiliary member 18 are adhered to each other by placing a liquid non-permeable sheet 19 made of polyethylene or the like between the two members. Though construction material of the absorption auxiliary member 18 can be selected from similar materials used in the absorption member 7, a hydrophilic polymer, a granular absorbent, a nonwoven fabric, a sponge material and the like may also be used because a hard raw material is not especially required in order to maintain the space.

FIGS. 5(*a*)–(*g*) illustrate examples of the observation window arranged on the base of the simplified measuring apparatus 1 of the present invention and of the signals to be formed on the reaction area, though these examples are in no way to be taken as limiting.

It is possible to obtain a plurality of signals by arranging plural reaction sites on the reaction area of the porous reaction membrane.

Examples of the shape formed on the reaction area include a cross 31, parallel lines 32, circles 33 and 34, a double circle 35, a star 36, a triangle 37 and the like.

In the case of an example of the use of a plurality of signals in which a substance to be assayed is used as a standard substance and linked in advance to one of the reaction sites, such as the shaded portion shown in FIGS. 5(*b*)–5(*e*), and 5(*g*), semi-quantitative or quantitative determination can be made by a single measuring operation by comparing their signal strengths.

An example of the use of the simplified measuring apparatus of the present invention in which an antibody is used as the affinity substance is described in the following with reference to the drawing of FIG. 1, by way of illustration and not by way of limitation.

In a process in which the simplified measuring apparatus 1 shown in FIG. 1 is used, a test sample is added dropwise to the opening 9 using a sterile pipette. The test sample passes through the porous body 4 containing a soluble agent adhered thereto in a releasable manner, where impurities suspended in the test sample are removed, the soluble agent is solubilized by the test sample and a substance to be assayed contained in the test sample is linked to the soluble agent. The resulting mixture solution migrates to the affinity substance immobilized porous reaction membrane 5, and the complex remains on the porous reaction membrane 5 when it is captured by the affinity substance specifically, while uncaptured contents pass through the porous reaction membrane 5 and are stored in the reaction solution storing space 16 arranged under the porous reaction membrane.

The thus stored reaction solution spreads on the transparent cover 8, migrates to the periphery of the cover and is finally absorbed by the absorption member 7. After a predetermined period of time (approximately 1 minute), the simplified measuring apparatus 1 is turned over to judge the presence or non-presence of a signal formed on the porous reaction membrane 5 by observing it through the opening 10 of the case 3. The presence of the substance to be assayed is judged by whether or not the signal is recognized.

EXAMPLES

The following measuring examples are provided to further illustrate the present invention. It is to be understood, however, that the examples are for purpose of illustration only and are not intended as a definition of the limits of the present invention.

Measuring Example 1 Measurement of hCG a) Purification of Anti-hCG Monoclonal Antibody Two hybridoma strains which have been obtained by a cell fusion method making use of polyethylene glycol in accordance with a procedure described in a method for an immunological experiments (*Men-eki Jikken Sohsa-ho*) VII 2211 (1978) were used in this example as strains capable of producing different monoclonal antibodies (to be referred to as "antibody A" and "antibody B" hereinafter) which recognize respectively different antigenic determinants on hCG. A 10 liter of culture filtrate prepared by culturing each of these strains was subjected to ammonium sulfate precipitation to obtain an IgG fraction which was subsequently purified by an affinity chromatography using a protein A Sepharose column. Antibodies A and B obtained in this way were separately dialyzed against physiological saline to yield 250 mg of antibody A and 245 mg of antibody B.

b) Preparation of a Soluble Agent

A 1 g of a disperse dye (RED VIOLET, manufactured by KAYARON) was suspended in 10 ml of distilled water and the suspension was centrifuged at 2,500×g for 10 minutes. The resulting supernatant fluid was centrifuged at 22,000×g for 10 minutes, and the thus obtained precipitate was suspended in 5 ml of distilled water to prepare a disperse dye for labeling. To 0.2 ml of the thus prepared disperse dye for labeling was added 0.2 ml of the antibody A which has been diluted with physiological saline to a concentration of 0.5 mg/ml, followed by 30 minutes of incubation at 56° C. After 20 minutes of cooling on an ice bath, the resulting reaction mixture was subjected to 10 minutes of centrifugation at 22,000×g, and the thus obtained precipitate was suspended in 0.5 ml of a 5% bovine serum albumin (to be referred to as "BSA" hereinafter)/10% lactose/0.076M Phosphate buffered saline pH6.4 (to be referred to as "PBS" hereinafter) solution to prepare a disperse dye-labeled anti-hCG antibody (to be referred to as "dye-labeled antibody A" hereinafter).

A gold colloid-labeled anti-hCG antibody (to be referred to as "gold colloid-labeled antibody A" hereinafter) was prepared by binding the anti-hCG antibody A to a gold colloid preparation manufactured by Biocell (particle size, 10 nm) in accordance with the procedure of Jan H. W. Leuvering et al. (*J. Immunol. Methods,* vol. 60, pp. 9–23, 1983).

A sheet of filter paper (No. 63, manufactured by Toyo Roshi) was cut into a disc of 14 mm in diameter, impregnated with 0.1 ml of the dye-labeled or gold colloid-labeled antibody A and then freeze-dried to prepare two soluble agent-adhered porous bodies.

c) Immobilization of Antibody to Porous Reaction Membrane

The antibody B diluted with physiological saline to a concentration of 2 mg/ml was applied to a nitrocellulose membrane having a pore size of 5 microns (manufactured by Toyo Roshi) and dried at 37° C. The thus treated membrane was blocked by soaking it in a 1% BSA/PBS solution to obtain the membrane of interest (to be referred to as "antibody B-immobilized membrane" hereinafter).

d) Construction of Measuring Apparatus

A measuring apparatus having the same structure shown in FIG. 1 was constructed by arranging the soluble agent-adhered porous body prepared in the above step b), the porous reaction membrane prepared in the above step c), a polypropylene-laminated sheet of a filter paper (No. 28, manufactured by Toyo Roshi) and a transparent polycarbonate plate having a thickness of 0.5 mm in order.

e) Measurement of hCG

Standard hCG solutions of 1,000, 500, 200, 100 and 50 mIU/ml were prepared by diluting an hCG standard reference material (in accordance with 3rd IS 75/537) with urine collected from a healthy male adult. A 0.5 ml of each of the thus prepared hCG standard solutions was added to the simplified measuring apparatus constructed in the above step d). When the test sample was completely absorbed by the absorption member (about 1 minute after the sample loading), development of color on the antibody B-immobilized membrane was judged by the naked eye from the backside of the measuring apparatus. Each test sample was judged positive (+) when color development was observed, or negative (−) when no color development was observed. The results are shown in Table 1.

TABLE 1

| Measurement of hCG | | | | | | |
|---|---|---|---|---|---|---|
| | Concentration of hCG (mIU/ml) | | | | | |
| | 0 | 50 | 100 | 200 | 500 | 1000 |
| Dye-labeled system | − | + | + | + | + | + |
| Gold colloid-labeled system | − | + | + | + | + | + |

Measuring Example 2 Measurement of LH a) Purification of Anti-LH Monoclonal Antibody Two hybridoma strains which have been obtained by a cell fusion method making use of polyethylene glycol in accordance with a procedure described in a method for an immunological experiments (*Men-eki Jikken Sohsa-ho*) VII 2211 (1978) were used in this example as strains capable of producing different monoclonal antibodies (to be referred to as "antibody C" and "antibody D" hereinafter) which recognize respectively different antigenic determinants on LH. A 10 liter of each culture filtrate prepared by culturing each of these strains was treated in the same manner as described in Measuring Example 1-a). Antibodies C and D obtained and purified in this way were separately dialyzed against physiological saline to yield 205 mg of antibody C and 255 mg of antibody D.

b) Preparation of a Soluble Agent

A 1 g of a disperse dye (RED VIOLET, manufactured by KAYARON) was suspended in 10 ml of distilled water and the suspension was centrifuged at 2,500×g for 10 minutes. The resulting supernatant fluid was centrifuged at 22,000×g for 10 minutes, and the thus obtained precipitate was suspended in 5 ml of distilled water to prepare a disperse dye for labeling. To 0.2 ml of the thus prepared disperse dye for labeling was added 0.2 ml of she antibody C which has been diluted with physiological saline to a concentration of 1 mg/ml, followed by 30 minutes of incubation at 56° C. After 20 minutes of cooling on an ice bath, the reaction mixture was subjected to 10 minutes of centrifugation at 22,000×g, and the thus obtained precipitate was suspended in 0.5 ml of a 5% BSA/10% lactose/PBS solution to prepare a disperse dye-labeled anti-LH antibody (to be referred to as "labeled antibody C" hereinafter).

A sheet of filter paper (No. 63, manufactured by Toyo Roshi) was cut into a disc of 14 mm in diameter, impregnated with 0.1 ml of the labeled antibody C and then freeze-dried to prepare freeze-dried labeled antibody C.

c) Immobilization of Antibody to Porous Reaction Membrane

At two positions within an area (about 12 mm in diameter) on a nitrocellulose membrane having a pore size of 5 microns (manufactured by Toyo Roshi), which corresponds to the reaction area of the present invention, different antibody solutions were dotted, each dot having a diameter of 3 mm. That is, at one of the two positions, the antibody D which has been diluted with physiological saline to a concentration of 2 mg/ml in the same manner as described in Measuring Example 1-c), was dotted, and dried at 37° C. As a positive control, at the other position, an anti-mouse IgG antibody in an amount which corresponds to the color developing of 50 mIU/ml of LH, was dotted, and dried in the same manner as described above. The thus treated membrane was blocked by soaking it in a 1% BSA/PBS solution to obtain the membrane of interest (to be referred to as "antibody D-immobilized membrane" hereinafter).

d) Construction of Measuring Apparatus

A measuring apparatus was constructed in the same manner as described in Measuring Example 1-d), by arranging the soluble agent-adhered porous body prepared in the above step b) and the porous reaction membrane prepared in the above step c).

e) Measurement of LH

Standard LH solutions of 200, 100 and 50 mIU/ml were prepared by diluting an LH standard reference material (UCB Bioproducts S.A., in accordance with Lutenizing Hormone 1st IRP 68/40) with urine collected from a healthy male adult. A 0.5 ml of each of the thus prepared LH standard solutions was added to the simplified measuring apparatus constructed in the above step d). When the test sample was completely absorbed by the absorption member (about 1 minute after the sample loading), development of color on the antibody D-immobilized membrane was judged by the naked eye from the backside of the measuring apparatus. Each test sample was judged positive (+) when a strong color development was observed, or negative (−) when no color development was observed or the color was weaker than that of the positive control. The results are shown in Table 2.

In addition, urine samples were collected daily from women having normal menstrual cycle and used as test samples for the measurement, with the results shown in Table 3.

TABLE 2

Measurement of LH

| | Concentration of LH (mIU/ml) | | | |
|---|---|---|---|---|
| | 0 | 50 | 100 | 200 |
| Judgement | − | + | + | + |

TABLE 3

Urine LH during menstrual cycle

| | Day | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Measurement | | | | | | | | | | | | | | | |
| Case 1 | − | − | − | − | − | − | − | − | − | − | − | − | + | + | + |
| Case 2 | − | − | − | − | − | − | − | − | − | − | − | + | + | − | − |

| | Day | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| Measurement | | | | | | | | | | | | | | | |
| Case 1 | − | − | − | − | − | − | − | − | − | − | − | − | − | − | − |
| Case 2 | − | − | − | − | − | − | − | − | − | − | − | − | − | − | − |

Measuring Example 3 Measurement of AFP in Vaginal Content a) Purification of Anti-AFP Monoclonal Antibody Two hybridoma strains which have been obtained by a cell fusion method making use of polyethylene glycol in accordance with a procedure described in a method for an immunological experiments (*Men-eki Jikken Sohsa-ho*) VII 2211 (1978) were used in this example as strains capable of producing different monoclonal antibodies (to be referred to as "antibody E" and "antibody F" hereinafter) which recognize respectively different antigenic determinants on AFP. A 10 liter of each culture filtrate prepared by culturing each of these strains was treated in the same manner as described in Measuring Example 1-a). Antibodies E and F obtained and purified in this way were separately dialyzed against physiological saline to yield 245 mg of antibody E and 250 mg of antibody F.

b) Preparation of a Soluble Agent

A 1 g of a disperse dye (Foron Brilliant Blue, manufactured by SANDOZ) was suspended in 10 ml of distilled water and the suspension was centrifuged at 2,500×g for 10 minutes. The resulting supernatant fluid was centrifuged at 22,000×g for 10 minutes, and the thus obtained precipitate was suspended in 5 ml of distilled water to prepare a disperse dye for labeling. To 0.2 ml of the thus prepared disperse dye for labeling was added 0.2 ml of the antibody E which has been diluted with physiological saline to a concentration of 1 mg/ml, followed by 30 minutes of incubation at 56° C. After 20 minutes of cooling on an ice bath, the resulting reaction mixture was subjected to 10 minutes of centrifugation at 22,000×g, and the thus obtained precipitate was suspended in 0.5 ml of a 5% BSA/10% lactose/PBS solution to prepare a disperse dye-labeled anti-AFP antibody (to be referred to as "labeled antibody E" hereinafter).

A sheet of filter paper (No. 63, manufactured by Toyo Roshi) was cut into a disc of 14 mm in diameter, impregnated with 0.1 ml of the labeled antibody E and then freeze-dried to prepare freeze-dried labeled antibody E.

c) Immobilization of an Antibody to a Porous Reaction Membrane

The antibody F diluted with physiological saline to a concentration of 2 mg/ml was applied to a nitrocellulose membrane and dried at 37° C. in the same manner as described in Measuring Example 1-c). The thus treated membrane was blocked by soaking it in a 1% BSA/PBS solution to obtain the membrane of interest (to be referred to as "antibody F-immobilized membrane" hereinafter).

d) Construction of Measuring Apparatus

A measuring apparatus having the same structure shown in FIG. 3 was constructed by arranging the soluble agent-adhered porous body prepared in the above step b), the porous reaction membrane prepared in the above step c), a sheet of filter paper (No. 28, manufactured by Toyo Roshi) having a laminated polyethylene layer on its one side and a hole of the same diameter as that of the reaction area on its central position and a transparent polycarbonate plate having a thickness of 0.3 mm in order.

e) Measurement of AFP

Standard AFP solutions of 5 and 20 ng/ml were prepared by diluting an AFP standard reference material (a-fetoprotein, manufactured by Cosmo Bio Co., Ltd.) with a 0.1% BSA/PBS solution. As test samples, an amniotic fluid sample containing known concentration of AFP was diluted with the 0.1% BSA/PBS solution to varied AFP concentrations of 50, 10, 2 and 0 ng/ml. Using two concentrations of the AFP standard solution per one concentration of the test sample as a set, 0.5 ml of each sample was added to the simplified measuring apparatus constructed in the above step d). Development of color on the antibody F-immobilized membrane was judged by the naked eye and measured using a color-difference meter (SZΣ 80, manufactured by Nippon Denshoku Kogyo Co., Ltd.) from the backside of the simplified measuring apparatus. Semi-quantitative and quantitative values were obtained by comparing simultaneously measured coloration of the 5 and 20 ng/ml standard solutions. Measured value by the color-difference meter was calculated by expressing the degree of coloration as a Lab-b value which was calculated from tristimulus values, X, Y and Z, based on the Hunter's equation and then comparing the Lab-b value with a standard curve. The Lab-b value becomes 10 in the case of no presence of color development and decreases as the intensity of blue color increases. When the value decreased to 8.0 or less, almost all of the panelists were able to recognize the blue color. The results are shown in Table 4.

TABLE 4

| Measurement of AFP | | | | |
|---|---|---|---|---|
| Standard solution | | | | |
| (ng/ml) | 5 | 20 | | |
| Lab-b | 5.5 | 0.5 | | |
| AFP concentration | | | | |
| (ng/ml) | 0 | 2 | 10 | 50 |
| Lab-b | 9.2 | 7.5 | 3.0 | −3.0 |
| Judged value | | | | |
| (ng/ml) | 0 | <5 | 5–20 | 20< |
| Measured value | | | | |
| (ng/ml) | 0 | 2 | 10 | 20< | g) Measurement of Vaginal Content

Samples of vaginal content were diluted with 0.1% BSA/PBS by a factor of 20, and the thus diluted test samples were measured in accordance with the reaction procedure described in Measuring Example 2-e). Results were judged with the naked eye based on the simultaneously measured coloration of a 5 ng/ml AFP standard solution. Clinically different test samples were collected from 15 cases of premature rupture of the membranes, 15 cases of normal pregnancy and 10 cases of amniotic fluid and carried out to measure. In the case of the premature rupture of the membranes and amniotic fluid, all samples showed a measured value of 100 ng/ml or more, while the value was less than 100 ng/ml in all of the cases of normal pregnancy. The results are shown in Table 5.

TABLE 5

| | Results of measurement | |
|---|---|---|
| Clinical results | 100 ng/ml or more | less than 100 ng/ml |
| Premature rupture of the membranes | 15/15 cases | 0/15 cases |
| Normal pregnancy | 0/15 cases | 15/15 cases |
| Amniotic fluid | 10/10 cases | 0/10 cases |

Thus, it is apparent that there has been provided, in accordance with the present invention, an apparatus for use in the simple and quick measurement of substances to be assayed, in which a porous reaction membrane is employed, as well as a measuring process making use of the simplified measuring apparatus. Development of the simplified measuring apparatus of the present invention has rendered possible qualitative or quantitative measurement of substances to be assayed, such as proteins, antibodies and the like, in a small amount of test samples by a simple and easy operation without requiring a B/F separation step.

What is claimed is:

1. A simplified measuring apparatus for use in a binding assay to determine the presence or amount of an analyte in a fluid test sample through the use of a label capable of producing a detectable response, said apparatus comprising:

(a) a porous body having releasably attached thereto an agent soluble in said test sample;

(b) a liquid permeable porous reaction membrane disposed below said porous body having defined thereon at least one reaction area, said reaction area having immobilized thereon an affinity substance capable of directly or indirectly capturing the analyte or an agent soluble in said test sample to thereby produce the detectable response;

(c) an absorption member disposed below said liquid permeable porous membrane having an opening being positioned below the reaction area of said liquid permeable porous membrane to define a reaction solution storing space within the opening, said absorption member being, arranged so as to contact only a peripheral area of said liquid permeable porous membrane via an intervening liquid impermeable sheet;

(d) a liquid impermeable transparent cover disposed below said opening of said absorption member; and (e) a liquid impermeable case accommodating said members (a), (b), (c) and (d) having a top surface adjacent said porous body and a bottom surface adjacent said transparent cover, said top surface having defined therein a top opening for introducing said fluid test sample, and said bottom surface having defined therein a bottom opening for observation of said detectable response.

2. A simplified measuring apparatus according to claim 1, wherein said reaction area comprises a plurality of reaction sites each having immobilized thereon an affinity substance different from other reaction sites.

3. A simplified measuring apparatus according to claim 2, wherein said plurality of reaction sites are separately defined from each other.

4. A simplified measuring apparatus according to claim 1, wherein said affinity substance immobilized on said liquid permeable porous reaction membrane is a member selected from the group consisting of an antibody and an antigen.

5. A simplified measuring apparatus according to claim 1, wherein said affinity substance immobilized on said liquid permeable porous reaction membrane is a member selected from the group consisting of a nucleic acid, a lectin, biotin, avidin, an enzyme, an inhibitor and a receptor.

6. A simplified measuring apparatus according to claim 1, wherein said agent soluble in said test sample is a member selected from the group consisting of an antibody and an antigen, that has been labeled with the label to produce the detectable response.

7. A simplified measuring apparatus according to claim 6, wherein said label is a member selected from the group consisting of an enzyme, a fluorescent compound, a radioactive label, a chemiluminescent compound, a colloidal metal particle, and a nonmetal particle.

8. A simplified measuring apparatus according to claim 7, wherein said label is a nonmetal particle selected from the group consisting of a dye particle, and a latex particle.

9. A simplified measuring apparatus according to claim 1, wherein said agent soluble in said test sample is a member selected from the group consisting of a nucleic acid, a lectin, biotin, avidin, an enzyme, an inhibitor and a receptor, that has been labeled with the label to produce the detectable response.

10. A simplified measuring apparatus according to claim 9, wherein said label is a member selected from the group consisting of an enzyme, a fluorescent compound, a radioactive label, a chemiluminescent compound, a colloidal metal particle, and a nonmetal particle.

11. A simplified measuring apparatus according to claim 10, wherein said label is a nonmetal particle selected from the group consisting of a dye particle, and a latex particle.

12. A simplified measuring apparatus according to claim 1, wherein said liquid permeable porous reaction membrane is a member selected from the group consisting of cellulose, a cellulose derivative, a porous synthetic polymer, a glass fiber filter, and a fabric.

13. A simplified measuring apparatus according to claim 12, wherein said liquid permeable porous reaction membrane is a cellulose derivative consisting of nitrocellulose.

14. A simplified measuring apparatus according to claim 1, wherein said porous body is a member selected from the group consisting of cellulose, a cellulose derivative, a porous synthetic polymer, a glass fiber filter, and a fabric.

15. A simplified measuring apparatus according to claim 1, wherein said absorption member is a member selected from the group consisting of cellulose, a cellulose derivative, a porous synthetic polymer, a glass fiber filter, a nonwoven fabric, a granular absorbent, and a fabric.

16. A simplified measuring apparatus according to claim 1, wherein said liquid permeable porous reaction membrane is nitrocellulose, and said absorption member and said porous body comprise cellulose.

17. A process for determining the presence or quantity of an analyte in a fluid test sample through the use of the simplified measuring apparatus of claim 1, comprising the steps of (a) adding the fluid test sample that is suspected to contain the analyte to the top opening defined on the top surface of the case to allow dissolution of said soluble agent releasably attached to said porous body and subsequent migration of the released agent to said porous liquid permeable reaction membrane;

(b) allowing said analyte, said released agent, or a complex thereof to contact with and bind to said affinity substance immobilized on the reaction area of said liquid permeable porous reaction membrane to thereby directly or indirectly produce the detectable response;

(c) allowing the fluid test sample added and said released agent that failed to become immobilized onto said liquid permeable porous reaction membrane to pass through said liquid permeable porous reaction membrane for absorption by said absorption member; and (d) observing said detectable response from said bottom opening on said bottom surface of the case to determine the presence or amount of the analyte in the fluid test sample.

18. A process according to claim 17, wherein said reaction area in said liquid permeable porous reaction membrane is washed to remove unbound materials.

19. A process according to claim 17, wherein said fluid test sample is a member selected from the group consisting of a body fluid, and a solution obtained by one of dissolving and extraction-diluting a biological component.

* * * * *